US00PP08069P

United States Patent [19]

Taylor

[11] Patent Number: Plant 8,069

[45] Date of Patent: Dec. 22, 1992

[54] PLUM TREE 'GREEN JADE'

[75] Inventor: James W. Taylor, Dinuba, Calif.

[73] Assignee: Ito Packing Company, Reedley, Calif.

[21] Appl. No.: 681,906

[22] Filed: Apr. 8, 1991

[51] Int. Cl.[5] ..... A01H 5/00

[52] U.S. Cl. ..... Plt./38.1

[58] Field of Search ..... Plt./38, 38.1

[56] References Cited

PUBLICATIONS

Anon, "Plum" (Wickson listings) *North American and European Fruit and Nut Tree Germplasm Resources Inventory* (1981) USDA Misc. Publ. No. 1406 p. 415.

Taylor, H. V., *The Plums of England* (1949) Crosby, Lockwood & Son, Ltd., London pp. 11, 12, 247 and 248.

*Primary Examiner*—James R. Feyrer

*Attorney, Agent, or Firm*—Dennis B. Haase

[57] ABSTRACT

A new plum tree of medium vigor, vase to spreading form, which bears blemish free cling stone fruit of attractive, uniform green exterior color with darker patterns of green flecks over a yellowish-green ground color at harvest, and which is of rounded shape, sweet subacid taste, and pronounced aroma and being ready for harvest in the last week of May when grown in the Reedley area of Fresno, Calif. Fruit is of excellent eating and shipping quality due to even ripening of light yellow flesh which has a few fibers and substantially uniform flesh color.

1 Drawing Sheet

BACKGROUND OF THE VARIETY

The present invention relates to a new and distinct variety of plum tree, which I refer to as Green Jade, of a yellow fleshed, cling stone fruit, green in color when mature in the early season period, which was developed from a continued fruit breeding program.

ORIGIN AND ASEXUAL REPRODUCTION OF THE NEW VARIETY

This invention was derived from an ongoing fruit breeding program to improve plums in regard to consumer quality and market acceptability. Seed from a Wickson seedling (not patented) were stratified and grown to a height of about 18 inches. These seedlings were bud grafted into dehorned orchard trees in the experimental orchard of Ito Packing Co., Inc., Reedley, Calif., for testing and selection. Each cone was budded into several limbs to make sure that it propagated true to type.

SUMMARY OF THE NEW VARIETY

The instant variety developed through the above method was selected because of its excellent eating quality and green color when mature in the early season.

BRIEF DESCRIPTION OF THE DRAWING

The accompanying drawing illustrates typical specimens of the fruit and foliage of my new variety as grown in the San Joaquin Valley of California. Three specimens of the fruit are shown, the upper left hand one of which is in the side elevation and adjacent thereto is a specimen shown from the apex view. A third specimen provided is a side elevation, sectioned to illustrate the internal texture and color of the flesh and pit. Finally, a characteristic twig and individual leaves are shown.

DETAILED DESCRIPTION

The following is a detailed description of my new plum variety with color reference being to the Maerz and Paul Dictionary of Colors, except in instances where terminology having generally accepted meaning is employed.

Parentage: Seeds from a Wickson seedling were grown bud grafted to dehorned orchard trees.

Propagation: Seedlings grown and bud grafted.

Locality where grown and observed: Near Reedley, Calif., County of Fresno, Calif.

TREE

Size: Average for species. The original tree grafted on a two-year old Lovell root stock is now 11 feet high and about 10 feet wide.

Vigor: Medium vigor. Growth can vary between 18 inches and 5 feet during the growing season depending on soil fertility, crop and pruning.

Regularity of bearing: Bears regularly on previous year's growth, as well as on spurs.

Trunk: Average for species. When compared with the main green fruited variety, Kelsey, this variety, Green Jade, is denser in foliage mainly because of closer distances between fruiting spurs and strong growth of the spurs.

Branches: Vase form but spreading as tree gets older. The angles of the main branches are slightly wider than that of the Kelsey variety. The variety is more vigorous, giving rise to more limbs within the tree's framework than in the Kelsey.

Leaves:

*Bark.*—Young limbs are grey but as the limbs get older the furrowed portions are of a slightly lighter brown than that of Kelsey.

*Color.*—Top side — 24L01; underside 31H10.

*Size.*—Average length of leaves on growth in general is of 8.2 cm; average width of 3.5 cm average length of leaves on spur growth — 5.8 cm and width of 2.0 cm.

*Shape.*—Lanceolate.

*Margin.*—Finely serriate.

*Glandular characteristics.*—Small, Globose, often one on either side of the petiole just below leaf blade; but there may be two on either side or none. Frequently there will be one on the leaf margin near the base.

*Petiole.*—Average for species.

*Glands.*—Small, globose; often one on either side of the petiole just below leaf blade, but there may be two on either side or none. Frequently, there will be one on the leaf margin near the base.

*Stipules.*—Very minute, dehiscent at a very young age.

Flower bud: Medium, white.

Flower: Medium size, white.

*Anthers.*—Yellow.

Time of full bloom: About one week ahead of the variety Santa Rosa. Full bloom in 1992 was February 26.

Pollenization: Can be pollenized by Santa Rosa and sets well when interplanted with Kelsey.

FRUIT

Maturity: When described, firm ripe, May 25.

Date of first picking: May 25.

Date of last picking: June 1.

Size: Average axial length, 5.4 cm; average transverse width in suture plane, 5.5 cm.

Form: Essentially round, but slightly compressed at the base.

*Suture.*—Smooth with very little depression.

*Ventral surface.*—Round.

*Cavity.*—Round, shallow.

*Base.*—Flattened slightly.

*Apex.*—Smooth although may be very slightly recessed in some fruit.

Skin:

*Thickness.*—Medium thick; medium texture.

*Tendency to crack.*—None observed.

*Bloom.*—Light.

*Color.*—At harvest time, green 19K9, with a more yellowish green (19L8) color developing as the fruit matures and finally turning a reddish color (13L6) over much of the surface in very soft ripe stage. The overall green speckling starts to turn red in the area around the apex when the fruit is left on the tree beyond the normal harvesting date. The fruit is too soft to market when the green specks and striations start to turn red over a greater portion of the fruit.

Flesh:

*Texture.*—Firm, juicy.

*Color.*—Light yellow (18B1) around inner part of the fruit darkening to 19F1 around outer portion of the fruit.

*Juice.*—Abundant.

*Flavor.*—Very sweet with pleasant acid balance.

*Aroma.*—Quite pronounced.

*Fibers.*—Few.

*Ripening.*—Evenly.

*Amygdalin.*—Slight amount present.

*Eating quality.*—Excellent.

Stone:

*Adherence to flesh.*—Generally clinging, but separates from the fruit around portions of the pit in some fruits.

*Size.*—Average thickness, 0.6 cm; average width, 1.6 cm; average length, 2.5 cm. The fruit is average in the market place.

*Form.*—Oval.

*Hilum.*—Small, oval

*Dorsal edge.*—Shallow groove, interrupted irregularity.

*Ventral edge.*—Wing continuous from near base to about ¼ inch from the apex.

*Surface.*—Irregularily pitted.

*Color.*—Light brown (12B6) with darker brown (13C8) areas as fruit matures.

Use: Fresh market.

Keeping quality: Excellent.

Shipping quality: Excellent.

Resistance to disease: Similar to other Japanese plum varieties.

Although this novel variety of plum tree possesses the described characteristics when grown in the Reedley area of Fresno County, Calif., in the central portion of the San Joaquin Valley, it is to be understood that some variations of the usual magnitude in characteristics incident to growing conditions elsewhere, fertilization, pruning and pest control are to be expected.

Having thus described and illustrated my new variety of plum tree, what is claimed as new and desired to be secured by Letters Patent is:

1. A new and distinct variety of plum tree of yellow fleshed, cling stone type, substantially as herein shown and described, having a maturity period in the early season and having fruit of good sugar content when harvested, with a green color.

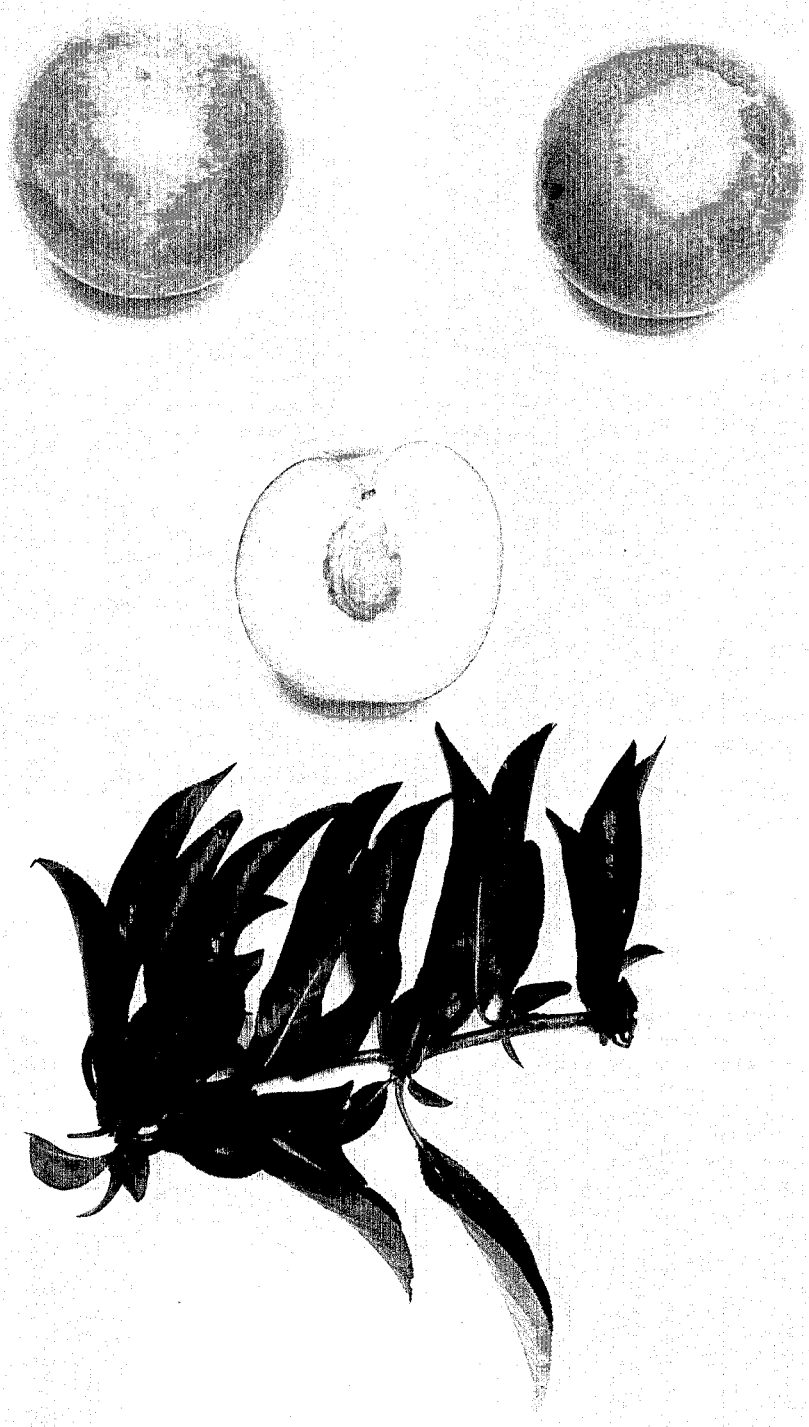

* * * * *